United States Patent [19]

Hansen et al.

[11] 4,451,378

[45] May 29, 1984

[54] ISOLATION OF 3-ISOPROPYL-2,1,3-BENZOTHIADIAZIN-4-ONE-2,2-DIOXIDE FROM WASTE WATER FROM ITS PREPARATION

[75] Inventors: Hanspeter Hansen; Hans Merkle; Albrecht Mueller, all of Ludwigshafen, Fed. Rep. of Germany

[73] Assignee: BASF Aktiengesellschaft, Ludwigshafen, Fed. Rep. of Germany

[21] Appl. No.: 434,369

[22] Filed: Oct. 14, 1982

[30] Foreign Application Priority Data

Oct. 19, 1981 [DE] Fed. Rep. of Germany ....... 3141428

[51] Int. Cl.$^3$ .............................................. C02F 1/54
[52] U.S. Cl. .................................... 210/725; 210/737; 210/909; 544/11
[58] Field of Search .............. 210/712, 714, 724, 725, 210/729, 737, 908, 909; 544/11

[56] References Cited

U.S. PATENT DOCUMENTS 4,284,516 8/1981 Parker et al. .................... 210/909
4,382,865 5/1983 Sweeny .......................... 210/909

*Primary Examiner*—Peter A. Hruskoci
*Attorney, Agent, or Firm*—Oblon, Fisher, Spivak, McClelland & Maier

[57] ABSTRACT

3-Isopropyl-2,1,3-benzothiadiazin-4-one-2,2-dioxide (bentazone) is isolated from waste water, originating from its preparation and working up, by treating the waste water with an acid to bring the pH initially to 7.5–9.5, adding 0.2–0.5% by volume, based on the waste water, of a 40–60 percent strength by weight aqueous bentazone salt solution and heating the mixture for 15–30 minutes at 75°–110° C. The solution thus treated is then cooled and brought to pH 1–3 with a mineral acid, whereupon the bentazone precipitates in a form which can be filtered off.

1 Claim, No Drawings

ISOLATION OF 3-ISOPROPYL-2,1,3-BENZOTHIADIAZIN-4-ONE-2,2-DIOXIDE FROM WASTE WATER FROM ITS PREPARATION

In preparing salts of 3-isopropyl-2,1,3-benzothiadiazin-4-one-2,2-dioxide, hereinafter refererred to by its common name of bentazone, the waste water obtained contains, as a consequence of the process, bentazone dissolved in the form of a salt, alongside inorganic salts, organic solvents and other by-products; for example, the bentazone salt may be the sodium or potassium salt or a trialkylammonium salt. Since bentazone is a valuable herbicide, it is desirable to isolate this residual salt. Such isolation is however in any case necessary in view of environmental protection regulations, calling for minimization of the chemical content of waste water.

The obvious methods, namely, after removal of solvents, simply to precipitate the bentazone with acids, failed inasmuch as the products obtained were gelatinous and could not be filtered.

It is an object of the present invention to remove the residual bentazone, dissolved in the form of salts, from the waste water, so as to be able to add it to the synthesized product.

We have found that this object is achieved, surprisingly, by heating the slightly alkaline waste water and adding a small amount of bentazone salts thereto before acidification, the process being defined in more detail in the claim.

Bentazone-containing waste water which can be treated according to the invention is obtained when bentazone is extracted from solutions of the crude active ingredient in organic solvents. For example, German Pat. No. 2,316,292 discloses a process of this type, and waste water resulting from this process is particularly suitable for the purposes of the invention.

In isolating bentazone in accordance with the invention, the procedure followed is first to bring the waste water obtained to a pH of 7.5–9.5, preferably 8–9, if it is not already at such a value. Depending on the initial pH, the pH may be adjusted by means of NaOH, ammonia or trialkanolamines, eg. triethanolamine, on the one hand, or with dilute $H_2SO_4$ or hydrochloric acid, on the other hand. To the solution thus adjusted is added 0.2–0.5% by volume, based on waste water, of a 40–60, preferabky 50, percent strength by weight aqueous solution of an alkali metal salt or ammonium salt of a bentazone advantageously obtained by the preceding synthesis, and the mixture is heated for 15–30, preferably 20–30, minutes at 75°–110° C., preferably 80°–105° C. It is then cooled to 5°–30° C., preferably room temperature, and the pH is brought to 1–3, preferably about 1.5, with a mineral acid, eg. $H_2SO_4$ or hyrochloric acid, whereupon the bentazone precipitates in a free form and can readily be filtered off.

We have found, surprisingly, that only with this combination of measures is satisfactory isolation of the bentazone from the waste water possible; if one of the measures is omitted, the filter becomes clogged on prolonged filtration.

Using the process according to the invention, it is possible to lower the bentazone content of the waste water by about 0.15–0.20% by weight, so the water then contains at most 0.03–0.025% by weight.

The bentazone thus obtained is 88–92% pure and is suitable for conversion to herbicide formulations.

The Examples which follow illustrate the invention.

COMPARATIVE EXAMPLE 1

(without addition of product)

12.2 parts of waste water from production were continuously introduced into a stirred flask equipped with an overflow, in such a way that the residence time was 30 minutes. The temperature was kept at 99°–100° C. The pH was kept at 8.5 by continuously adding 15% strength $H_2SO_4$ (0.29 part).

The waste water thus pretreated passed, via the overflow and a cooling zone, into a second vessel, kept at 20° C. There, the pH was lowered to 1.5 by further addition of 15% strength $H_2SO_4$ (0.95 part), and the 3-isopropyl-2,1,3-benzothiadiazin-4-one-2,2-dioxide, present in the waste water as a salt, was thereby precipitated. The residence time was again 30 minutes. The material leaving the precipitation flask was fed directly onto a suction filter.

After about 2 hours, the fabric of the suction filter began to clog, since the gelatinous product obtained was no longer filterable.

The product obtained was 54.4% pure.

EXAMPLE (according to the invention)

0.062 part of an aqueous solution containing 50% of 3-isopropyl-2,1,3-benzothiadiazin-4-one-2,2-dioxide as the sodium salt, was added to 12.2 parts of waste water and the mixture was then treated further as described in Comparative Example 1.

After the experiment had run for 48 hours, no deterioration in filtration rate was found. The 0.183% content of 3-isopropyl-2,1,3-benzothiadiazin-4-one-2,2-dioxide in the feed (before addition of the 50% strength) solution) was lowered to 0.028% in the filtrate.

The product obtained was 89.6% pure.

COMPARATIVE EXAMPLE 2

(without heat treatment)

0.062 part of an aqueous solution containing 50% of 3-isopropyl-2,1,3-benzothiadiazin-4-one-2,2-dioxide as the sodium salt was added to 12.2 parts of waste water.

This solution was introduced, at 20° C., into a stirred flask with overflow, in such a way that the residence time was 30 minutes. The pH was kept at 8.5 by continuous addition of 15% strength $H_2SO_4$ (0.29 part). The waste water thus pretreated passed via the overflow into a second flask. There, the pH was lowered to 1.5, at 20° C., by further addition of 15% strength $H_2SO_4$ (0.95 part), and the 3-isopropyl-2,1,3-benzothiadiazin-4-one-2,2-dioxide, dissolved as a salt in the waste water, was thereby precipitated, The residence time was again 30 minutes. The material leaving the precipitation flask was fed directly onto a suction filter.

After about 5 hours the filtration rate dropped and after 10 hours the experiment had to be discontinued since the product formed had clogged the filter fabric. The product obtained was 68.6% pure.

We claim:

1. A process for isolating 3-isopropyl-2,1,3-benzothiadizin-4-one-2,2-dioxide (bentazone) from waste water containing bentazone which comprises:
   (a) adjusting the pH of said waste water to a pH in the range of 7.5 to 9.5 and adding about 0.2 to 0.5% by volume, based on the waste water, of about a 40 to 60% by weight aqueous solution of an alkali metal salt or ammonium salt of bentazone;

(b) heating the mixture for about 15 to 30 minutes, at a temperature in the range of 75° to 115° C.;

(c) cooling said mixture to a temperature in the range of 5° to 30° C.; and (d) adjusting the pH of the cooled mixture to a pH in the range of 1 to 3 with a mineral acid, to precipitate the bentazone in a free form, thereby allowing the filtration of said precipitate.

* * * * *